(12) United States Patent
Germain et al.

(10) Patent No.: US 10,568,685 B2
(45) Date of Patent: Feb. 25, 2020

(54) ARTHROSCOPIC DEVICES AND METHODS

(71) Applicant: RELIGN Corporation, Cupertino, CA (US)

(72) Inventors: Aaron Germain, San Jose, CA (US); Kyle Klein, San Jose, CA (US); Michael D. Walker, San Francisco, CA (US)

(73) Assignee: RELIGN Corporation, Campbell, CA (US)

( * ) Notice: Subject to any disclaimer, the term of this patent is extended or adjusted under 35 U.S.C. 154(b) by 110 days.

(21) Appl. No.: 15/415,721

(22) Filed: Jan. 25, 2017

(65) Prior Publication Data

US 2017/0128083 A1 May 11, 2017

Related U.S. Application Data

(63) Continuation of application No. 14/960,084, filed on Dec. 4, 2015, now Pat. No. 9,585,675.

(Continued)

(51) Int. Cl.
*A61B 17/16* (2006.01)
*A61B 18/14* (2006.01)
(Continued)

(52) U.S. Cl.
CPC ........ *A61B 18/148* (2013.01); *A61B 17/1615* (2013.01); *A61B 17/1626* (2013.01); *A61B 17/1628* (2013.01); *A61B 17/1631* (2013.01); *A61B 17/1633* (2013.01); *A61B 17/1637* (2013.01); *A61B 17/32002* (2013.01); *A61B 2017/0023* (2013.01); *A61B 2017/00039* (2013.01); *A61B 2017/0088* (2013.01);
(Continued)

(58) Field of Classification Search
CPC .......... A61B 17/1615; A61B 17/32002; A61B 17/1617; A61B 17/1666; A61B 17/1668
See application file for complete search history.

(56) References Cited

U.S. PATENT DOCUMENTS

| 2,513,564 A | 7/1950 | Ingwersen |
| 2,514,545 A | 7/1950 | Ingwersen |

(Continued)

FOREIGN PATENT DOCUMENTS

| DE | 102005059864 A1 | 6/2007 |
| EP | 1034747 A1 | 9/2000 |

(Continued)

OTHER PUBLICATIONS

Co-pending U.S. Appl. No. 15/855,684, filed Dec. 27, 2017.
(Continued)

*Primary Examiner* — Olivia C Chang
(74) *Attorney, Agent, or Firm* — Wilson Sonsini Goodrich & Rosati

(57) ABSTRACT

A medical device includes an elongated sleeve having a longitudinal axis, a proximal end and a distal end. A cutting member extends distally from the distal end of the elongated sleeve, and has sharp cutting edges. The cutting head is formed from a wear-resistant ceramic material, and a motor coupled to the proximal end of elongated sleeve rotate the cutting member. The cutter is engaged against bone and rotated to cut bone tissue without leaving any foreign particles in the site.

6 Claims, 12 Drawing Sheets

Related U.S. Application Data

(60) Provisional application No. 62/250,315, filed on Nov. 3, 2015, provisional application No. 62/245,796, filed on Oct. 23, 2015.

(51) Int. Cl.
*A61B 17/32* (2006.01)
*A61B 17/00* (2006.01)
*A61B 17/22* (2006.01)
*A61B 18/00* (2006.01)

(52) U.S. Cl.
CPC ............... *A61B 2017/00473* (2013.01); *A61B 2017/00836* (2013.01); *A61B 2017/22079* (2013.01); *A61B 2017/320028* (2013.01); *A61B 2018/00577* (2013.01); *A61B 2018/00601* (2013.01); *A61B 2018/00702* (2013.01); *A61B 2018/142* (2013.01); *A61B 2217/005* (2013.01); *A61B 2217/007* (2013.01); *A61B 2218/007* (2013.01)

(56) References Cited

U.S. PATENT DOCUMENTS

| | | |
|---|---|---|
| 2,625,625 A | 1/1953 | Ingwersen |
| 2,689,895 A | 9/1954 | Ingwersen |
| 3,611,023 A | 10/1971 | Souza, Jr. et al. |
| 3,838,242 A | 9/1974 | Goucher |
| 3,848,211 A | 11/1974 | Russell |
| 3,868,614 A | 2/1975 | Riendeau |
| 3,903,891 A | 9/1975 | Brayshaw |
| 4,060,088 A | 11/1977 | Morrison, Jr. et al. |
| 4,272,687 A | 6/1981 | Borkan |
| 4,781,175 A | 11/1988 | McGreevy et al. |
| 4,895,146 A | 1/1990 | Draenert |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,449,356 A | 9/1995 | Walbrink et al. |
| 5,490,854 A | 2/1996 | Fisher et al. |
| 5,602,449 A | 2/1997 | Krause et al. |
| 5,641,251 A | 6/1997 | Leins et al. |
| 5,669,907 A | 9/1997 | Platt, Jr. et al. |
| 5,683,366 A | 11/1997 | Eggers et al. |
| 5,720,745 A | 2/1998 | Farin et al. |
| 5,759,185 A | 6/1998 | Grinberg |
| 5,766,195 A | 6/1998 | Nobles |
| 5,776,092 A | 7/1998 | Farin et al. |
| 5,810,809 A | 9/1998 | Rydell |
| 5,823,971 A | 10/1998 | Robinson et al. |
| 5,839,897 A | 11/1998 | Bordes |
| 5,849,010 A | 12/1998 | Wurzer et al. |
| 5,857,995 A * | 1/1999 | Thomas ............ A61B 17/1615 604/22 |
| 5,873,855 A | 2/1999 | Eggers et al. |
| 5,888,198 A | 3/1999 | Eggers et al. |
| 5,891,095 A | 4/1999 | Eggers et al. |
| 5,904,681 A | 5/1999 | West, Jr. |
| 5,913,867 A | 6/1999 | Dion |
| 5,964,752 A | 10/1999 | Stone |
| 5,989,248 A | 11/1999 | Tu et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,245,084 B1 | 6/2001 | Mark et al. |
| 6,261,241 B1 | 7/2001 | Burbank et al. |
| 6,296,636 B1 | 10/2001 | Cheng et al. |
| 6,332,886 B1 | 12/2001 | Green et al. |
| 6,348,051 B1 | 2/2002 | Farin et al. |
| 6,358,263 B2 | 3/2002 | Mark et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,443,948 B1 | 9/2002 | Suslov |
| 6,475,215 B1 | 11/2002 | Tanrisever |
| 6,538,549 B1 | 3/2003 | Renne et al. |
| 6,579,289 B2 | 6/2003 | Schnitzler |
| 6,610,059 B1 | 8/2003 | West et al. |
| 6,632,220 B1 | 10/2003 | Eggers et al. |
| 6,656,195 B2 | 12/2003 | Peters et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,783,533 B2 | 8/2004 | Green et al. |
| 6,821,275 B2 | 11/2004 | Truckai et al. |
| 6,837,884 B2 | 1/2005 | Woloszko |
| 6,890,332 B2 | 5/2005 | Truckai et al. |
| 6,902,564 B2 | 6/2005 | Morgan et al. |
| 6,979,332 B2 | 12/2005 | Adams |
| 7,087,054 B2 | 8/2006 | Truckai et al. |
| 7,150,747 B1 | 12/2006 | McDonald et al. |
| 7,220,261 B2 | 5/2007 | Truckai et al. |
| 7,309,849 B2 | 12/2007 | Truckai et al. |
| 7,549,989 B2 | 6/2009 | Morgan et al. |
| 7,674,263 B2 | 3/2010 | Ryan |
| 7,678,069 B1 | 3/2010 | Baker et al. |
| 7,713,269 B2 | 5/2010 | Auge, II et al. |
| 7,717,710 B2 | 5/2010 | Danger et al. |
| 7,744,595 B2 | 6/2010 | Truckai et al. |
| 7,771,422 B2 | 8/2010 | Auge et al. |
| 7,819,861 B2 | 10/2010 | Auge et al. |
| 7,819,864 B2 | 10/2010 | Morgan et al. |
| 7,955,331 B2 | 6/2011 | Truckai et al. |
| 8,012,153 B2 | 9/2011 | Woloszko et al. |
| 8,016,823 B2 | 9/2011 | Shadduck |
| 8,062,319 B2 | 11/2011 | O'Quinn et al. |
| 8,075,555 B2 | 12/2011 | Truckai et al. |
| 8,192,424 B2 | 6/2012 | Woloszko |
| 8,192,428 B2 | 6/2012 | Truckai et al. |
| 8,221,404 B2 | 7/2012 | Truckai |
| 8,323,280 B2 | 12/2012 | Germain et al. |
| 8,333,763 B2 | 12/2012 | Truckai et al. |
| 8,702,702 B1 | 4/2014 | Edwards et al. |
| 9,179,923 B2 | 11/2015 | Gubellini et al. |
| 9,204,918 B2 | 12/2015 | Germain et al. |
| 9,277,954 B2 | 3/2016 | Germain et al. |
| 9,504,521 B2 | 11/2016 | Deutmeyer et al. |
| 9,585,675 B1 | 3/2017 | Germain et al. |
| 9,592,085 B2 | 3/2017 | Germain et al. |
| 9,603,656 B1 | 3/2017 | Aaron et al. |
| 9,795,434 B2 | 10/2017 | Germain et al. |
| 10,022,140 B2 | 7/2018 | Germain et al. |
| 2002/0038129 A1* | 3/2002 | Peters ............ A61B 17/32002 606/167 |
| 2003/0014051 A1 | 1/2003 | Woloszko |
| 2003/0083681 A1 | 5/2003 | Moutafis et al. |
| 2003/0125727 A1 | 7/2003 | Truckai et al. |
| 2003/0163135 A1 | 8/2003 | Hathaway |
| 2004/0044341 A1 | 3/2004 | Truckai et al. |
| 2004/0167427 A1 | 8/2004 | Quick et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |
| 2006/0074345 A1 | 4/2006 | Hibner |
| 2006/0178670 A1 | 8/2006 | Woloszko et al. |
| 2006/0200123 A1 | 9/2006 | Ryan |
| 2006/0224154 A1 | 10/2006 | Shadduck et al. |
| 2007/0213704 A1 | 9/2007 | Truckai et al. |
| 2008/0003255 A1 | 1/2008 | Kerr et al. |

(56) References Cited

U.S. PATENT DOCUMENTS

| | | | |
|---|---|---|---|
| 2008/0103494 | A1 | 5/2008 | Rioux et al. |
| 2008/0188848 | A1 | 8/2008 | Deutmeyer et al. |
| 2008/0208249 | A1* | 8/2008 | Blain ................ A61B 17/1608 |
| | | | 606/207 |
| 2009/0048485 | A1 | 2/2009 | Heisler |
| 2009/0076498 | A1 | 3/2009 | Saadat et al. |
| 2009/0270849 | A1 | 10/2009 | Truckai et al. |
| 2010/0100091 | A1 | 4/2010 | Truckai |
| 2010/0305565 | A1 | 12/2010 | Truckai et al. |
| 2011/0282373 | A1 | 11/2011 | Chekan et al. |
| 2012/0209112 | A2 | 8/2012 | Patel; Himanshu N et al. |
| 2012/0245580 | A1 | 9/2012 | Germain et al. |
| 2012/0330292 | A1 | 12/2012 | Shadduck et al. |
| 2013/0122461 | A1 | 5/2013 | Shioiri |
| 2013/0172870 | A1 | 7/2013 | Germain et al. |
| 2013/0267937 | A1 | 10/2013 | Shadduck et al. |
| 2013/0296847 | A1 | 11/2013 | Germain et al. |
| 2013/0296849 | A1 | 11/2013 | Germain et al. |
| 2013/0317493 | A1 | 11/2013 | Truckai et al. |
| 2013/0331833 | A1 | 12/2013 | Bloom |
| 2014/0100567 | A1 | 4/2014 | Edwards et al. |
| 2014/0336643 | A1 | 11/2014 | Orczy-Timko et al. |
| 2016/0346036 | A1 | 12/2016 | Orczy-Timko et al. |
| 2019/0015151 | A1 | 1/2019 | Germain et al. |

FOREIGN PATENT DOCUMENTS

| | | |
|---|---|---|
| WO | WO-0053112 A2 | 9/2000 |
| WO | WO-0062685 A1 | 10/2000 |
| WO | WO-0053112 A3 | 12/2000 |
| WO | WO-2007073867 A1 | 7/2007 |
| WO | WO-2017136414 A1 | 8/2017 |

OTHER PUBLICATIONS

Notice of allowance dated Mar. 19, 2018 for U.S. Appl. No. 15/421,264.
Office action dated Jul. 6, 2018 for U.S. Appl. No. 15/449,796.
Office Action dated Jul. 21, 2017 for U.S. Appl. No. 15/421,264.
Office action dated Nov. 3, 2017 for U.S. Appl. No. 15/449,796.
Co-pending U.S. Appl. No. 15/421,264, filed Jan. 31, 2017.
Co-pending U.S. Appl. No. 15/449,796, filed Mar. 3, 2017.
Co-pending U.S. Appl. No. 15/599,372, filed May 18, 2017.
European search report dated Nov. 2, 2009 for EP Application No. 01967968.7.
International search report and opinion dated Jul. 15, 2016 for PCT/US2016/027157.
International Search Report and Written Opinion dated Mar. 8, 2017 for International PCT Patent Application No. PCT/US2016/058179.
International Search Report and Written Opinion dated May 16, 2017 for International PCT Patent Application No. PCT/US2017/016002.
International search report and written opinion dated May 23, 2012 for PCT/US2012/023390.
International Search Report and Written Opinion dated Nov. 29, 2016 for International Application No. PCT/US2016/058145.
International search report dated Jan. 14, 2002 for PCT/US2001/025409.
Kim, et al. Optical feedbacksignal for ultra short pulse ablation of tissue. Appl. Surface Sci. 1998; 127-129:857-862.
Notice of Allowance dated Jan. 6, 2017 for U.S. Appl. No. 14/960,084.
Notice of Allowance dated Feb. 8, 2017 for U.S. Appl. No. 14/977,256.
Notice of Allowance dated Feb. 16, 2017 for U.S. Appl. No. 15/096,546.
Notice of Allowance dated Dec. 2, 2016 for U.S. Appl. No. 14/977,256.
Notice of Allowance dated Dec. 30, 2016 for U.S. Appl. No. 14/977,256.
Office action dated May 3, 2016 for U.S. Appl. No. 14/960,084.
Office action dated Jul. 28, 2016 for U.S. Appl. No. 14/977,256.
Office Action dated Aug. 18, 2016 for U.S. Appl. No. 14/960,084.
Office action dated Sep. 26, 2016 for U.S. Appl. No. 15/096,546.
Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.
Tucker et al. Histologic characteristics of electrosurgical injuries. J. Am. Assoc. Gyneco. Laproscopy. 1997; 4(2):857-862.
Volpato, et al., Application of Zirconia in Dentistry: Biological, Mechanical and Optical Considerations. Advances in ceramics-electric and magnetic ceramics, bioceramics, ceramics and environment. Sep. 2011.
Notice of allowance dated Feb. 4, 2019 for U.S. Appl. No. 15/449,796.
Notice of allowance dated Mar. 7, 2019 for U.S. Appl. No. 15/449,796.

\* cited by examiner

ARTHROSCOPIC DEVICES AND METHODS

CROSS-REFERENCE TO RELATED APPLICATIONS

This application is a continuation of U.S. patent application Ser. No. 14/960,084, filed Dec. 4, 2015, now U.S. Pat. No. 9,585,675, which claims the benefit of provisional application 62/250,315, filed on Nov. 3, 2015, and of provisional application 62/245,796, filed on Oct. 23, 2015, the full disclosures of which are incorporated herein by reference.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments configured for cutting and removing bone or other hard tissue and having a ceramic cutting member.

2. Description of the Background Art

In several surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove tissue for such procedures. A typical arthroscopic shaver or burr comprises a metal cutting member carried at the distal end of a metal sleeve that rotates within an open-ended metal shaft. A suction pathway for removal of bone fragments or other tissues is provided through a window proximal to the metal cutting member that communicates with a lumen in the sleeve.

When metal shavers and burrs "wear" during a procedure, which occurs very rapidly when cutting bone, the wear can be accompanied by loss of micro-particles from fracture and particle release which occurs along with dulling due to metal deformation. In such surgical applications, even very small amounts of such foreign particles that are not recovered from a treatment site can lead to detrimental effects on the patient health, with inflammation being typical. In some cases, the foreign particles can result in joint failure due to osteolysis, a term used to define inflammation due to presence of such foreign particles. A recent article describing such foreign particle induced inflammation is Pedowitz, et al. (2013) Arthroscopic surgical tools: "A source of metal particles and possible joint damage", Arthroscopy—The Journal of Arthroscopic and Related Surgery, 29(9), 1559-1565. In addition to causing inflammation, the presence of metal particles in a joint or other treatment site can cause serious problems for future MRIs. Typically, the MRI images will be blurred by agitation of the metal particles caused by the magnetic field used in the imaging, making assessments of the treatment difficult.

Another problem with the currently available metal shavers/burrs relates to manufacturing limitations in combination with the rapid dulling of metal cutting edges. Typically, a metal cutter is manufactured by machining the cutting surfaces and flutes into a burr or abrader surface. The flute shape and geometry can be limited since it is dictated by the machining process, and burr size and shape limitations may direct usage toward more coarse bone removal applications. Further, when operated in a rotational or oscillatory mode, the cutting edges adapted for coarse bone removal may have a kickback effect as the flutes first make contact with bone, which is aggravated by rapid dulling of the machined cutting edges.

Therefore, the need exists for arthroscopic burrs and/or shavers that can operate to cut and remove bone without the release of fractured particles and micro-particles into the treatment site. Further, there is a need for burrs/cutters that do not wear rapidly and that can have cutting edges not limited by metal machining techniques.

SUMMARY OF THE INVENTION

The present invention provides a high-speed rotating cutter or burr that is fabricated entirely of a ceramic material. In one variation, the ceramic is a molded monolith with sharp cutting edges and is adapted to be motor driven at speeds ranging from 3,000 rpm to 20,000 rpm. The ceramic cutting member is coupled to an elongate inner sleeve that is configured to rotate within a metal, ceramic or composite outer sleeve. The ceramic material is exceptionally hard and durable and will not fracture and thus not leave foreign particles in a treatment site. In one aspect, the ceramic has a hardness of at least 8 GPa ($kg/mm^2$) and a fracture toughness of at least 2 $MPam^{1/2}$. The "hardness" value is measured on a Vickers scale and "fracture toughness" is measured in $MPam^{1/2}$. Fracture toughness refers to a property which describes the ability of a material containing a flaw to resist further fracture and expresses a material's resistance to such fracture. In another aspect, it has been found that materials suitable for the cutting member of the invention have a certain hardness-to-fracture toughness ratio, which is a ratio of at least 0.5 to 1.

While the cutting assembly and ceramic cutting member of the invention have been designed for arthroscopic procedures, such devices can be fabricated in various cross-sections and lengths and can be use in other procedures for cutting bone, cartilage and soft tissue such as in ENT procedures, spine and disc procedures and plastic surgeries.

In a first specific aspect, the present invention provides a medical device includes an elongated sleeve having a longitudinal axis, a proximal end and a distal end. A cutting member extends distally from the distal end of the elongated sleeve, and has sharp cutting edges. The cutting head is formed from a wear-resistant ceramic material, and a motor coupled to the proximal end of elongated sleeve rotates the cutting member. The cutter may be engaged against bone and rotated to cut bone tissue without leaving any foreign particles in the site.

The wear-resistant ceramic material may comprise any one or combination of (1) zirconia, (2) a material selected from the group of yttria-stabilized zirconia, magnesia-stabilized zirconia and zirconia toughened alumina, or (3) silicon nitride. The cutting member typically has from 2 to 100 cutting edges, a cylindrical periphery, and is usually rounded in the distal direction. The cutting member will typically have diameter ranging from 2 mm to 10 mm, and the cutting edges will typically extend over an axial length ranging between 1 mm and 10 mm. The cutting edges may be any one of helical, angled or straight relative to said axis, and flutes between the cutting edges usually have a depth ranging from 0.10 mm to 2.5 mm. An aspiration tube may be configured to connect to a negative pressure source, where the cutting member has at least one window in a side thereof which opens to a hollow interior. In these embodiments, the hollow interior is open to a central passage of the elongated member which is connected to the aspiration tube.

In a further aspect, the present invention provides a medical device for treating bone including an elongated shaft having a longitudinal axis, a proximal end, and a distal end. A monolithic cutting member fabricated of a material having a hardness of at least 8 GPa (kg/mm$^2$) is coupled to the distal end of the elongated shaft, and a motor is operatively connected to the proximal end of the shaft, said motor being configured to rotate the shaft at at least 3,000 rpm.

The material usually has a fracture toughness of at least 2 MPam$^{1/2}$, and further usually has a coefficient of thermal expansion of less than 10 (1×10$^6$/° C.). The material typically comprises a ceramic selected from the group of yttria-stabilized zirconia, magnesia-stabilized zirconia, ceria-stabilized zirconia, zirconia toughened alumina and silicon nitride, and the cutting member typically has a cylindrical periphery and an at least partly rounded periphery in an axial direction.

In a still further aspect, the present invention provides a medical device for treating bone comprising a monolithic cutting member fabricated of a material having a hardness-to-fracture toughness ratio of at least 0.5:1, usually at least 0.8:1, and often at least 1:1.

In yet another aspect, the present invention provides a medical device for cutting tissue including a motor-driven shaft having a longitudinal axis, a proximal end, a distal end, and a lumen extending therebetween. A rotatable cutting member is fabricated entirely of a ceramic material and is operatively coupled to the distal end of the motor-driven shaft. At least one window in the cutting member communicates with the lumen in the shaft, and a negative pressure source is in communication with the lumen to remove cut tissue from an operative site.

The ceramic material typically has a hardness of at least 8 GPa (kg/mm$^2$) and a fracture toughness of at least 2 MPam$^{1/2}$. Additionally, the ceramic material will usually have a coefficient of thermal expansion of less than 10 (1×10$^6$/° C.). Exemplary ceramic materials are selected from the group consisting of yttria-stabilized zirconia, magnesia-stabilized zirconia, ceria-stabilized zirconia, zirconia toughened alumina and silicon nitride, and the cutting member usually has cutting edges where the at least one window is proximate to the cutting edges, and the at least one window is in at least one flute between the cutting edges.

In another aspect, the present invention provides a method for preventing foreign particle induced inflammation at a bone treatment site. A rotatable cutter fabricated of a ceramic material having a hardness of at least 8 GPa (kg/mm$^2$) and a fracture toughness of at least 2 MPam$^{1/2}$, is engaged against bone and rotated to cut bone tissue without leaving any foreign particles in the site.

The ceramic material is usually selected from the group consisting of yttria-stabilized zirconia, magnesia-stabilized zirconia, ceria-stabilized zirconia, zirconia toughened alumina and silicon nitride, and the cutter is typically rotated at 10,000 rpm or greater. Cut bone tissue is removed from the bone treatment site through a channel in the cutter, typically by aspirating the cut bone tissue through the channel.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and removal devices and related methods of use. Several variations of the invention will now be described to provide an overall understanding of the principles of the form, function and methods of use of the devices disclosed herein. In general, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, the present invention provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 rpm to 20,000 rpm.

Figure 1:
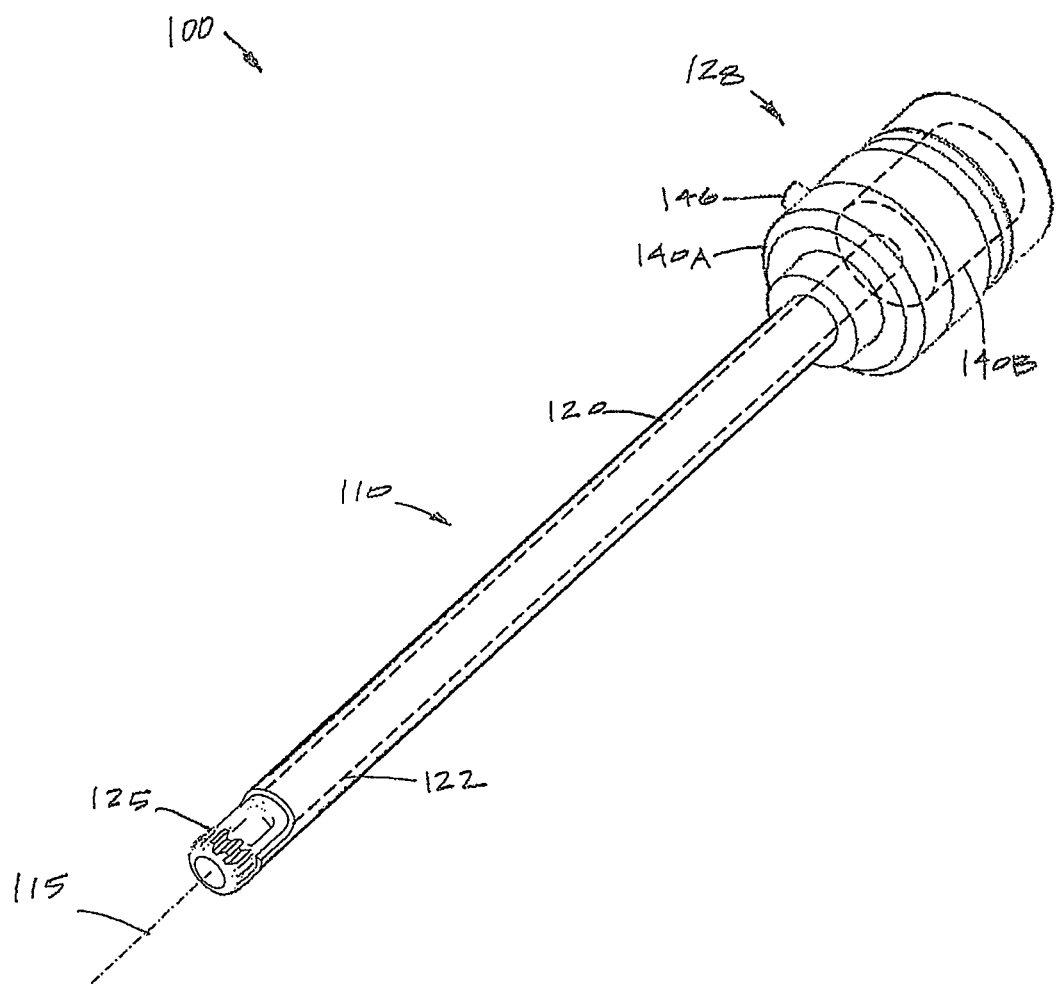
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
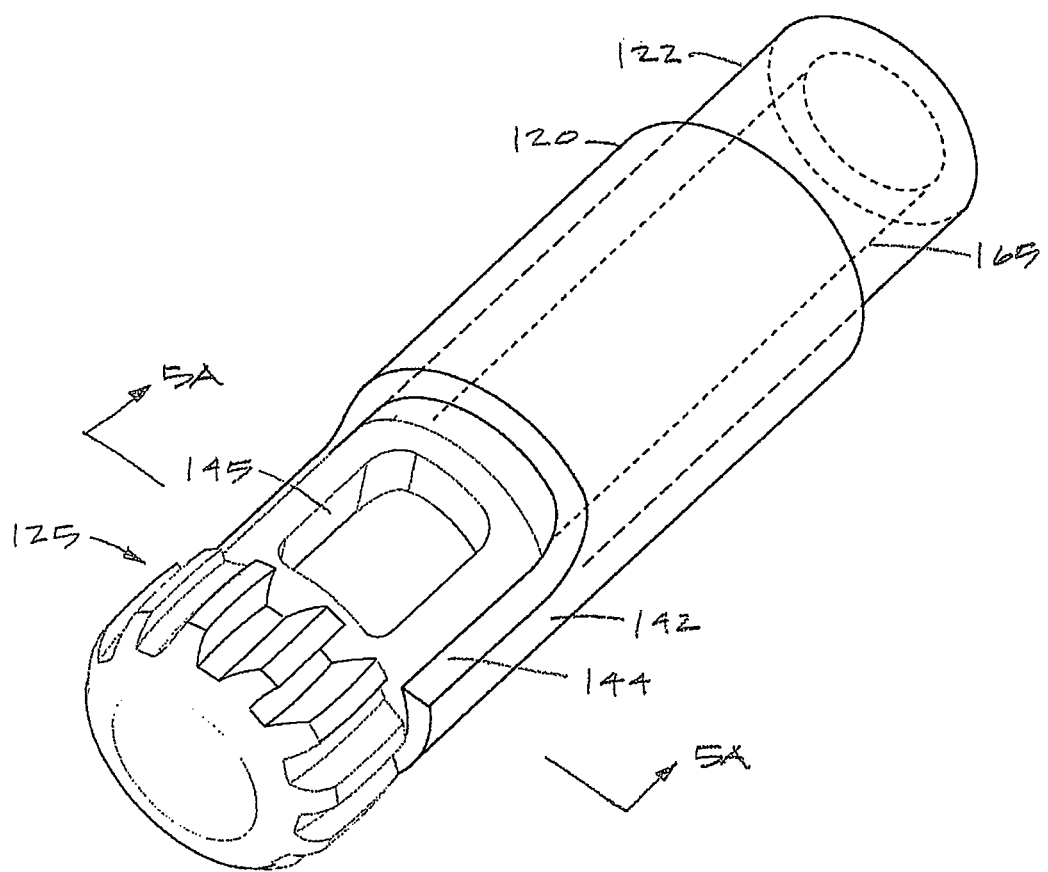
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in a manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 ands 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104. As can be seen in FIG. 1, the outer hub 140A includes a projecting key 146 that is adapted to mate with a receiving J-lock slot 148 in the handle 104 (see FIG. 3).

Figure 3:
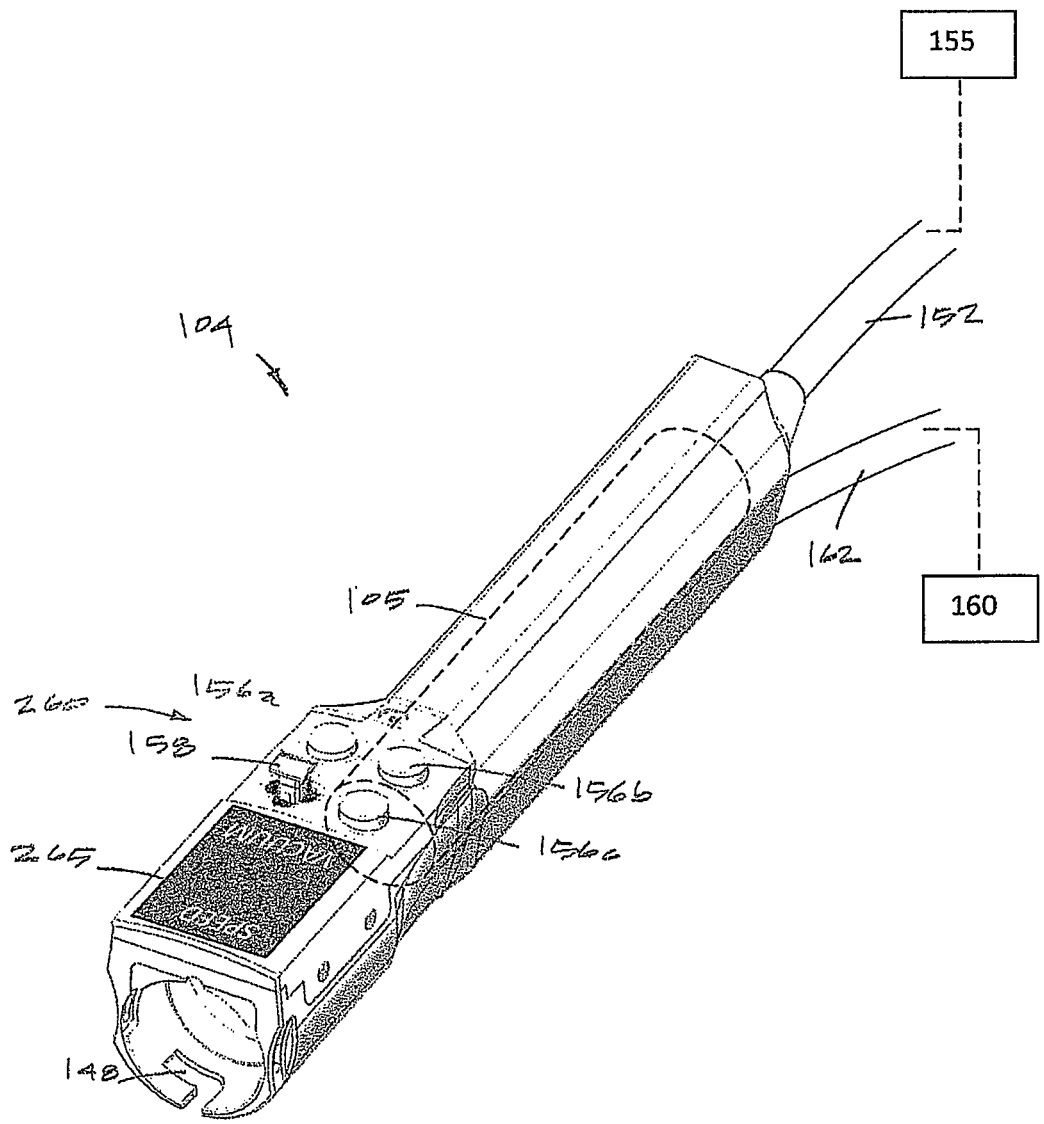
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 be moved forward and backward to adjust the rotational speed of the ceramic cutting member 125. The rotational speed of the cutter can continuously adjustable, or can be adjusted in increments up to 20,000 rpm. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
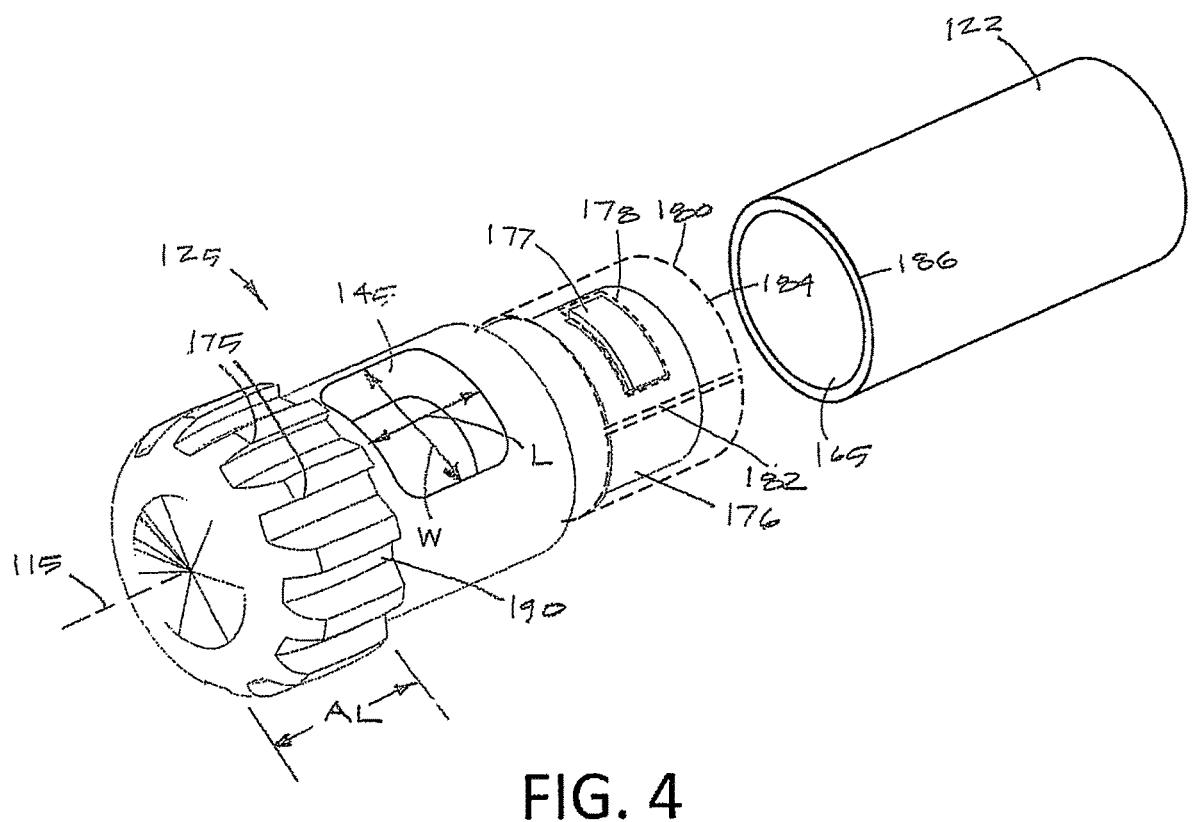
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

| | Hardness (GPa) | Fracture Toughness $(MPam^{1/2})$ | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) | | | |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) | | | |
| Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) | | | |
| YTA-14 (Superior Technical Ceramics) | 14.0 | 5 | 2.80:1 |
| ZTA (CoorsTek) | 14.8 | 6 | 2.47:1 |
| Ceria stabilized zirconia | | | |
| CSZ (Superior Technical Ceramics) | 11.7 | 12 | 0.98:1 |
| Silicon Nitride | | | |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics— Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used may be selected from the group consisting of magnesia-stabilized zirconia, ceria-stabilized zirconia, zirconia toughened alumina and silicon nitride. In general, in one aspect of the invention, the monolithic ceramic cutting member 125 has a hardness rating of at least 8 GPa (kg/mm$^2$). In another aspect of the invention, the ceramic cutting member 125 has a fracture toughness of at least 24 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 (1×10$^6$/° C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
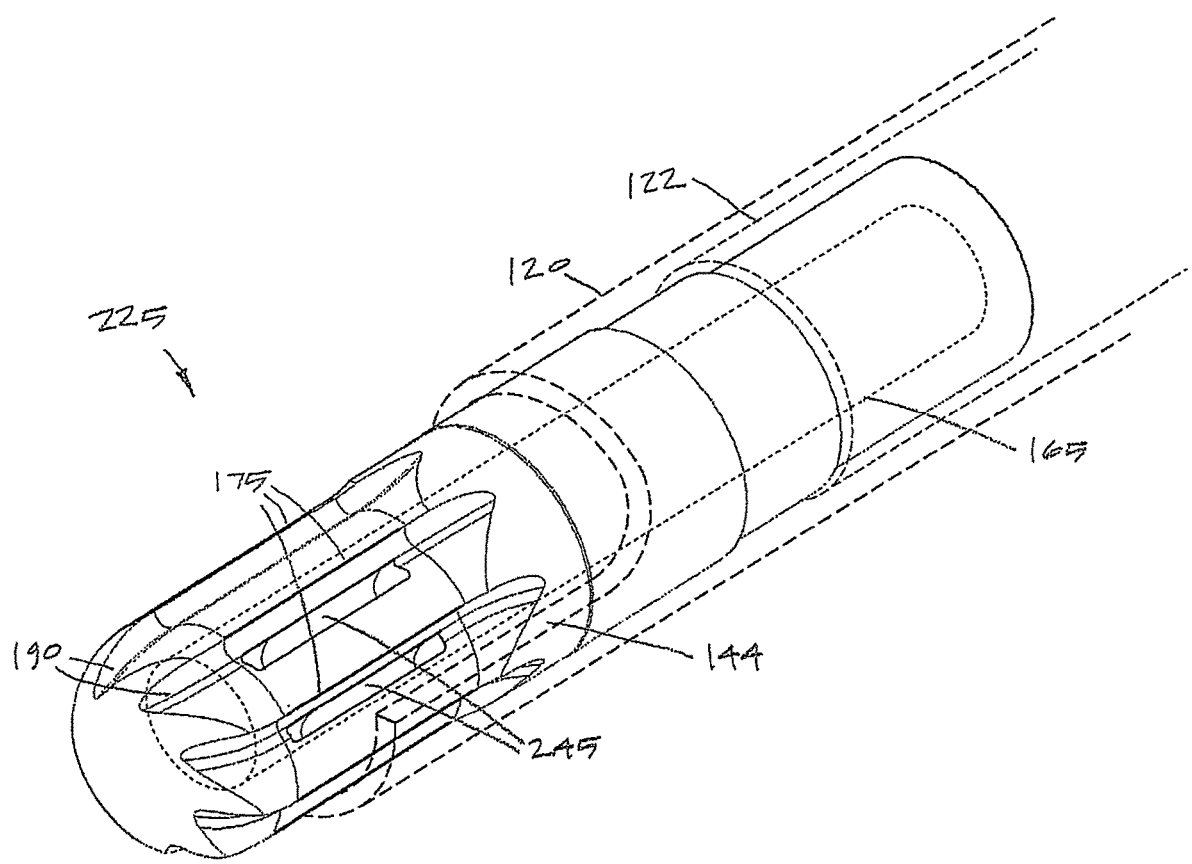
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
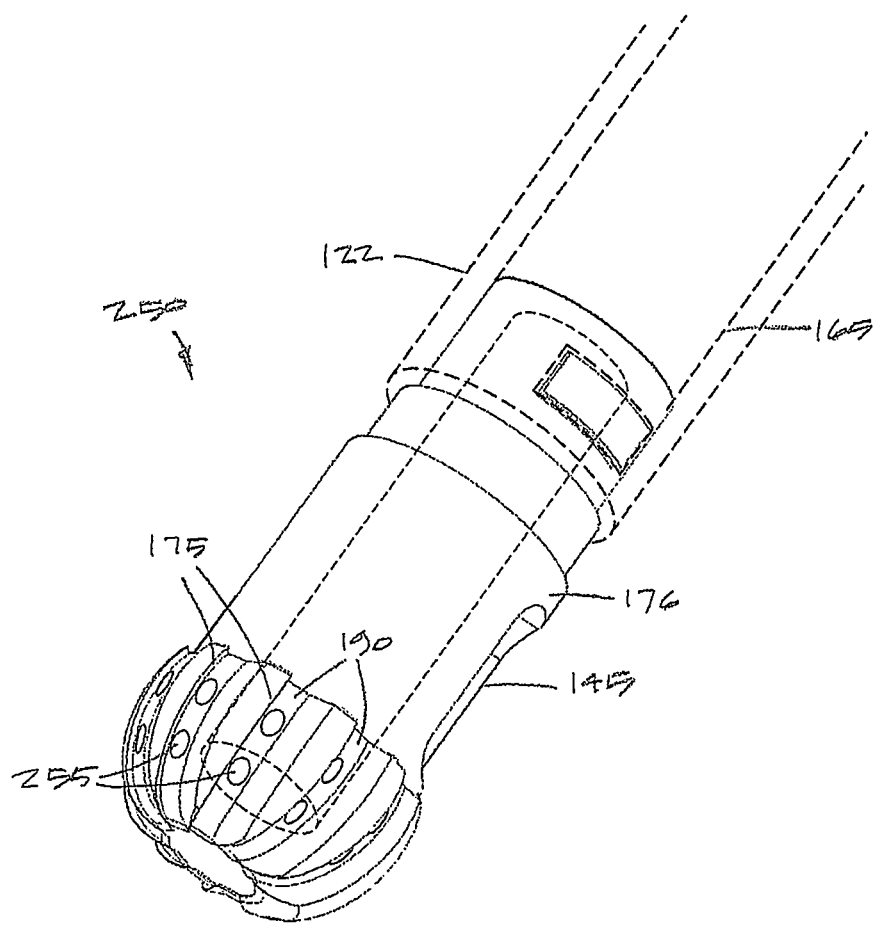
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 ands intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
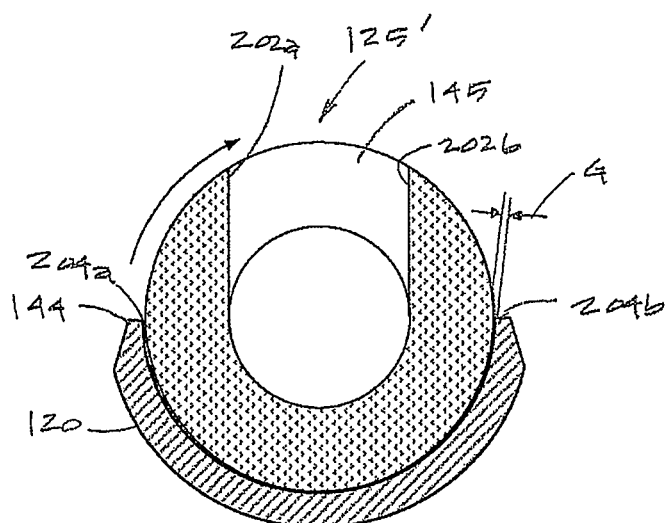
FIG. 5A is a cross-sectional view of a cutting assembly similar to that of FIG. 2 taken along line 5A-5A showing the close tolerance between sharp cutting edges of a window in a ceramic cutting member and sharp lateral edges of the outer sleeve which provides a scissor-like cutting effect in soft tissue.
Figure 5B:
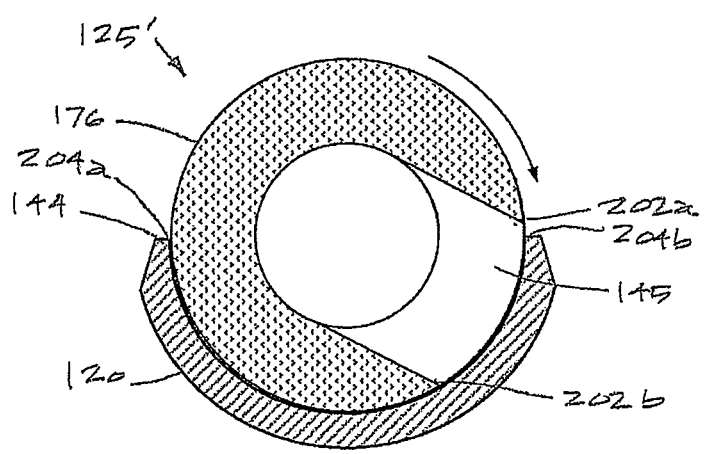
FIG. 5B is a cross-sectional view of the cutting assembly of FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020", or less than 0.010".

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 GPa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
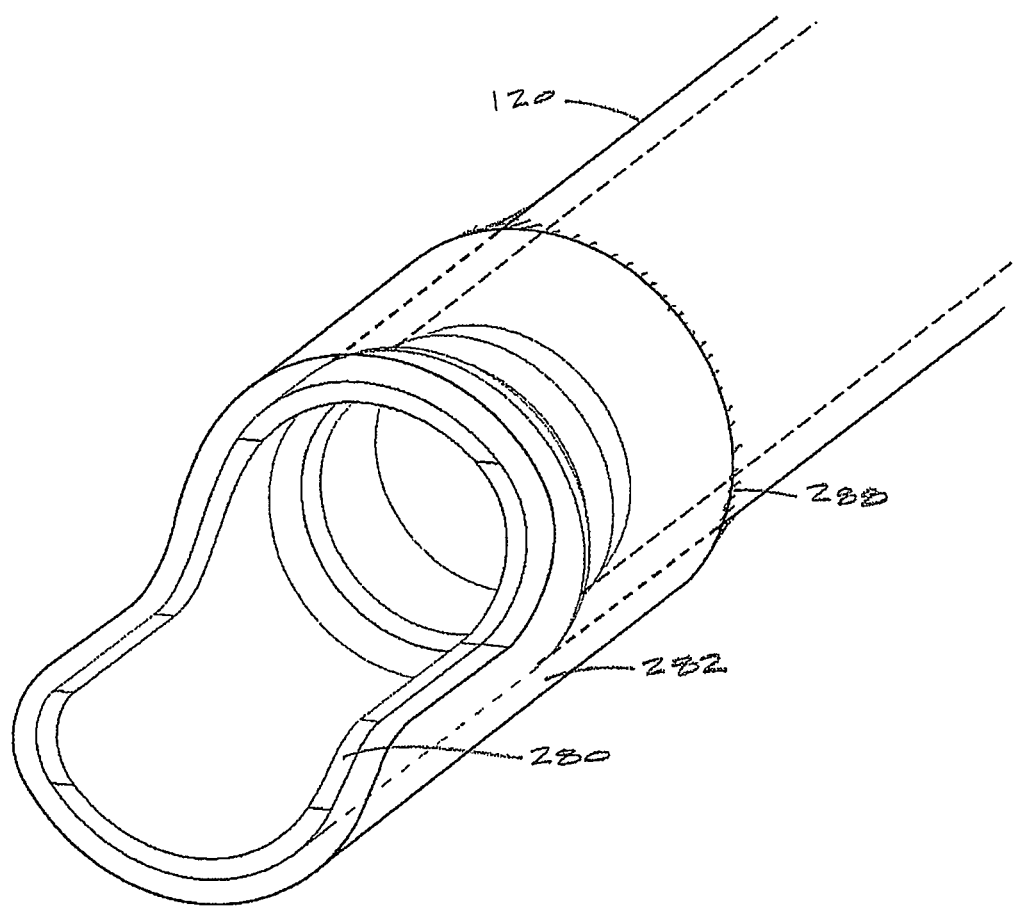
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9A:
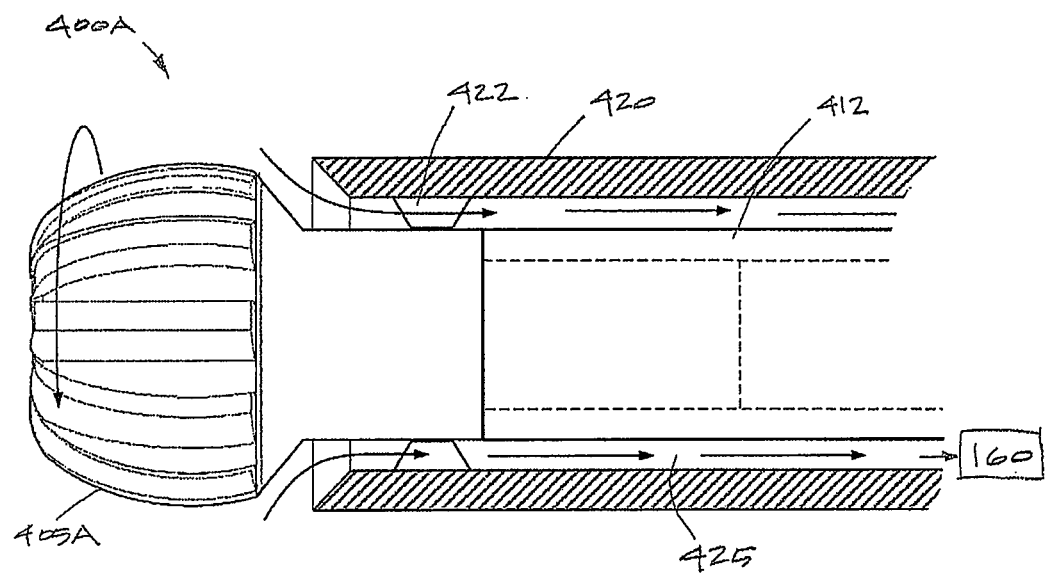
FIG. 9A is a side cut-away view of a ceramic cutting member and shaft illustrating an aspiration pathway in the assembly.

FIGS. 9A-9D illustrate variations of cutter assemblies 400A-400D that include ceramic cutters 405A-405C with various fluid inflow and fluid outflow channels that can be incorporated into the assembly. FIG. 9A illustrates a cutter assembly 400A with a monoblock ceramic cutter 405A coupled to inner sleeve 412 that rotates in outer sleeve 420. The outer sleeve 420 can be a ceramic, metal, polymer or combination thereof and includes a plurality of three to ten collar elements 422 in the bore 425 in which the inner sleeve 412 and ceramic cutter rotate. The negative pressure source 160 described above is connected to bore 425 to aspirate fluid and tissue debris through the gaps (indicated by arrows) between the collar elements 422 outwardly to a collection reservoir.

Figure 9B:
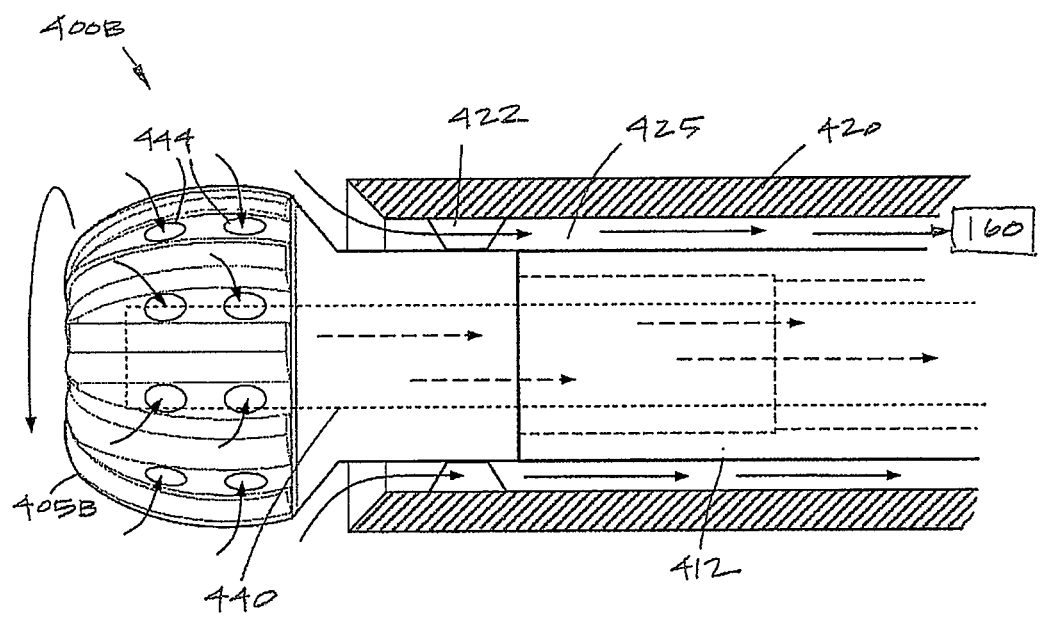
FIG. 9B is a cut-away view of an alternative working end and ceramic cutting member illustrating multiple aspiration pathways in the assembly.
Figure 9C:
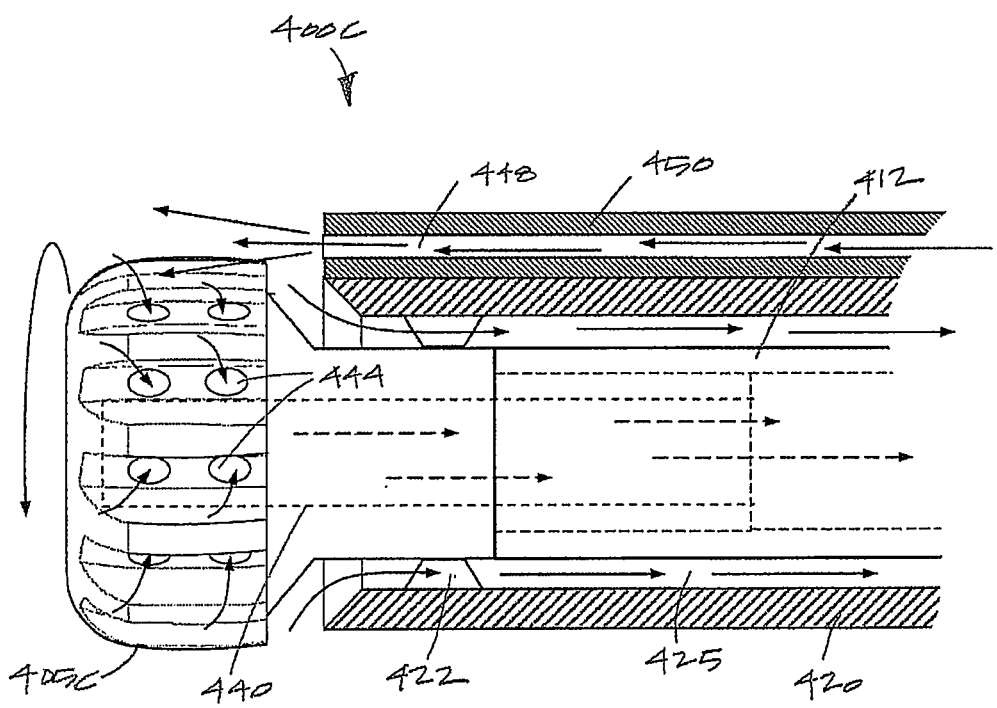
FIG. 9C is a cut-away view of an alternative working end and ceramic cutting member illustrating both inflow and aspiration pathways in the assembly.

FIG. 9B illustrates another variation of cutter assembly 400B that is similar to the version of FIG. 9A except that the ceramic cutting member 405B has an interior flow channel 440 that communicates with openings 444 in the surface of the cutting member. In this variation, the negative pressure source 160 is connected to flow channel 440 in the ceramic cutter 405B to thus aspirate fluid and tissue debris through the cutter (indicated by arrows) as well as through bore 425 in outer sleeve 420. FIG. 9C illustrates another variation of cutter assembly 400C that is similar to that of FIG. 9B except that a fluid inflow channel 448 is provided in a hypotube 450 coupled to the exterior of outer sleeve 420. The fluid inflow can be low pressure, high pressure and/or pulsed to infuse the treatment site with fluid.

Figure 9D:
FIG. 9D is a cut-away view of another variation of working end and ceramic cutting member illustrating both inflow and aspiration pathways in the assembly.

FIG. 9D illustrates a variation of cutter assembly 400D that is similar to that of FIG. 9B except that ceramic cutting member 405D has an interior flow channel 460 that communicates with openings 464 and a fluid inflow source is coupled thereto for providing fluid inflows through the ceramic cutting member 405D as indicated by arrows. The fluid outflows are provided through bore 425 in outer sleeve 420 as described previously.

Figure 10:
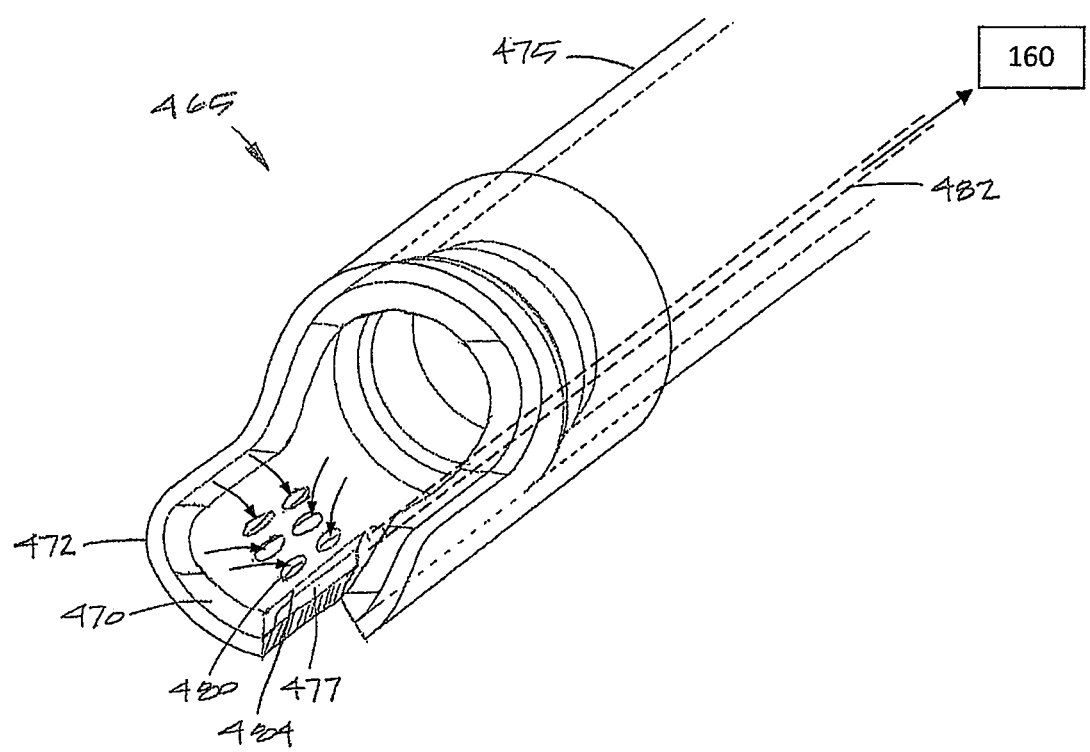
FIG. 10 is a perspective cut-away view of ceramic housing carried by an outer sleeve illustrating an aspiration or inflow pathway.

FIG. 10 illustrates another variation of an outer sleeve assembly 465 without showing the rotating ceramic cutter. The variation of FIG. 10 is similar to that of FIG. 8 and includes a ceramic housing 470 carried in an outer metal housing 472 coupled to outer sleeve 475. In this variation, the ceramic housing 470 has a flow channel 477 and ports 480 formed therein that communicate with a negative pressure source 160 to aspirate fluid as indicated by the arrows in FIG. 10. The channel 477 extends proximally though a flow passageway 482 in the wall of outer sleeve 475. In one variation, the ceramic housing 470 can comprise a resilient ceramic with wall portion 484 molded so as to be biased against a rotating ceramic cutter. In another variation, fluid inflows could be provided through flow channel 477 and ports 480.

Figure 11:
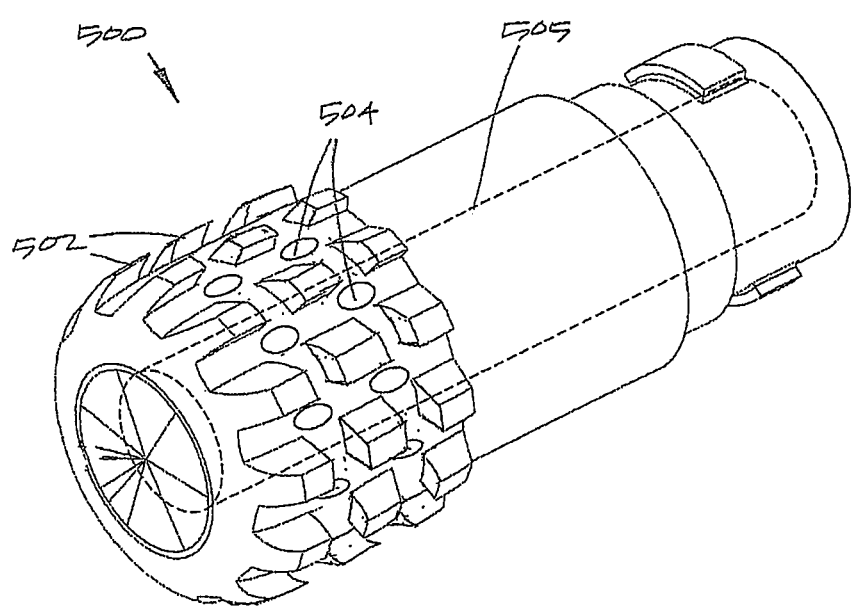
FIG. 11 is a perspective of a variation of a ceramic cutting member illustrating with multiple abrading teeth.

FIG. 11 illustrates another variation of a ceramic cutting member 500 that has a plurality of abrading teeth 502, ports 504 and an interior flow channel 505 which can be fabricated as described above by a ceramic molding process. A complex part as shown in FIG. 11 would be expensive to fabricate from a metal, such as stainless steel.

In another embodiment (not shown) a cutting member can be fabricated of corundum. Corundum is a crystalline form of aluminum oxide which may have various colors, and which generally is referred to as sapphire. The terms "corundum" and "sapphire" may be used interchangeably herein to refer to the crystalline form of aluminum oxide. A monolithic, monocrystal cutting member could be made from a sapphire and falls within the scope of the invention, and would be most suitable for simple cutting elements as fabrication costs would be high for any complex shapes. Similarly, silica and silica borate and other forms of glass fall within the scope of the invention.

Now referring to FIG. 3, the handle 104 can be a conventional non-disposable component and includes a control panel 260 that is adapted to allow simplified manual (thumb) control of multiple functions of the device together with an LCD display 265 that can provide the physician with visual information about operating parameters.

In one variation, the joystick 158 can be used to actuate the motor drive and also to control its speed and direction of rotation. In a variation, the joystick 158 is adapted for movement in four directions and also can be depressed downwardly to actuate a function. In one variation, the joystick 158 can be pushed downward to activate the motor drive and released to de-activate the motor drive. The joystick 158 can be moved forward and backward relative to the axis of handle 104 to either increase or decrease the speed of the motor. In such a variation, movement of joystick 158 to the left or to the right can increase or decrease fluid inflow/outflow rates from a fluid management system associated with an arthroscopic procedure.

The control panel 260 further includes push buttons 156a, 156b and 156c that can be used to select various operational modes, such as selection of forward (clockwise) rotating mode, selection of backward (counter-clockwise) rotating mode, selection of intermittent forward or backward rotating mode, selection of oscillating mode, selection of level of aspiration through an extraction channel of the device, selection of inflows such as a flush mode and the like.

In another embodiment, a cutting system as shown in FIGS. 1, 3, 4, 6 and 8A-8D can have a controller that is operatively coupled to both the motor 105 and the negative pressure source 160 (see FIG. 3) to control rotational speed of the ceramic cutting member as well as to control the negative pressure level. In a variation, the controller includes an algorithm that modulates negative pressure and thus fluid outflows in response to the rotational speed of the ceramic cutting member. For example, an algorithm can increase negative pressure and fluid outflows as the speed of the cutter increases to thereby remove greater volumes of fluid and tissue debris. In one system embodiment, the controller can control a fluid outflow pump and a fluid inflow pump, and the speed of the outflow pump (and negative pressure) can be modulated in response to the rotational speed of the cutter. In this system variation, the controller also can control the inflow pump to increase fluid inflows into a treatment site in response to increases in the rotational speed of the cutter, or in response to the increase in speed of the outflow pump.

A number of embodiments of the invention have been described. Nevertheless, it will be understood that various modifications may be made without departing from the spirit and scope of the invention.

What is claimed is:

1. A method of preventing metal particle induced inflammation in a joint treatment site comprising;
    providing a cutting device comprising (i) an inner sleeve that carries a distal rotatable cutter fabricated from a ceramic material having a hardness of at least 8 Gpa (kg/mm$^2$) and a fracture toughness of at least 2 M Pam$^{1/2}$, the cutter having a window with a pair of opposed lateral sides each having a cutting edge, wherein said window opens to a central channel therein that communicates with a negative pressure source, and (ii) an outer sleeve fabricated from a metal having a distal cut-out portion with lateral edges, wherein said distal cut-out portion is rotationally aligned with cutter window;
    rotating the inner sleeve within the outer sleeve to pass the cutting edges of the window past the lateral edges of the distal cut-out portion to cut tissue therebetween, wherein a gap between the cutting edges of the window and the lateral edges of the cut-out portion of the metal outer sleeve as the cutting edges pass the lateral edges is less than 0.020"; and
    activating the negative pressure source to extract tissue chips through the window and the central channel and into the collection reservoir.

2. The method of claim 1, wherein the ceramic material is selected from the group consisting of yttria-stabilized zirconia, magnesia-stabilized zirconia, ceria-stabilized zirconia, zirconia toughened alumina and silicon nitride.

3. The method of claim 1, wherein the cutter is rotated at 3,000 rpm or greater.

4. The method of claim 1, further comprising engaging the window with cutting edges against soft tissue while rotating the inner sleeve to cut soft tissue.

5. The method of claim 4, wherein the cutting device further comprises sharp cutting edges formed distally of the window, further comprising engaging the sharp cutting edges against bone while rotating the inner sleeve to remove bone tissue.

6. The method of claim 5, wherein the cutter is rotated at 10,000 rpm or greater.

* * * * *